US009872526B2

(12) United States Patent
Safran et al.

(10) Patent No.: US 9,872,526 B2
(45) Date of Patent: Jan. 23, 2018

(54) BRACE FOR PREVENTING SYMPTOMS OF FEMORAL ACETABULAR IMPINGEMENT

(71) Applicants: Marc Safran, Stanford, CA (US); Tomoo Yamada, Cupertino, CA (US)

(72) Inventors: Marc Safran, Stanford, CA (US); Tomoo Yamada, Cupertino, CA (US)

(*) Notice: Subject to any disclaimer, the term of this patent is extended or adjusted under 35 U.S.C. 154(b) by 738 days.

(21) Appl. No.: 13/714,035

(22) Filed: Dec. 13, 2012

(65) Prior Publication Data
US 2014/0165264 A1 Jun. 19, 2014

(51) Int. Cl.
*A41D 1/08* (2006.01)
*A61F 5/01* (2006.01)

(52) U.S. Cl.
CPC .............. *A41D 1/08* (2013.01); *A61F 5/0193* (2013.01)

(58) Field of Classification Search
CPC .. A41D 1/08; A41D 2300/22; A41D 13/0015; A41D 13/0506; A41D 13/0543; A41D 1/06; A41D 2300/20; A61F 5/0104; A61F 5/0106; A61F 5/0109; A61F 5/0193; A61F 5/0102; A61F 2005/0165; A63B 21/04; A63B 21/0407; A63B 21/4025
USPC ...... 2/69, 79, 227, 228, 238; 602/23, 24, 26, 602/62, 63; 482/121, 124
See application file for complete search history.

(56) References Cited

U.S. PATENT DOCUMENTS

| | | |
|---|---|---|
| 3,035,586 A | 5/1962 | Bell |
| 5,109,546 A | 5/1992 | Dicker |
| 5,201,074 A | 4/1993 | Dicker |
| 5,857,947 A | 1/1999 | Dicker et al. |
| 5,937,441 A | 8/1999 | Raines |
| 5,968,002 A | 10/1999 | Morrisseau |
| 6,231,488 B1 | 5/2001 | Dicker et al. |
| 6,401,497 B1 | 6/2002 | Nishiyama et al. |

(Continued)

FOREIGN PATENT DOCUMENTS

| | | |
|---|---|---|
| CN | 2449679 Y | 9/2001 |
| CN | 2577798 Y | 10/2003 |

(Continued)

OTHER PUBLICATIONS

PCT International Application No. PCT/US2013/075181, International Search Report and Written Opinion, dated Mar. 25, 2014.

(Continued)

*Primary Examiner* — Amy Vanatta
(74) *Attorney, Agent, or Firm* — Kilpatrick Townsend & Stockton LLP

(57) ABSTRACT

Tension members anchored to a wearer's body to resist femoral acetabular impingement (FAI)-causing movements. A first tension member is anchored to the body of a subject, and produces a force on the subject's body to primarily limit the ability of the subject's thigh to internally rotate and the ability of the subject's knee to adduct. Thus, this first tension member resists the tendency of the subject's leg to twist inward or deflect inward, each of which may contribute to FAI. A second tension member is anchored to the subject's body, and provides a force to the subject's body to primarily limit the ability of the subject's hip joint to move in flexion. Thus, the second tension member resists the tendency of the subject's leg to raise too high, which may also contribute to FAI.

8 Claims, 2 Drawing Sheets

(56) References Cited

U.S. PATENT DOCUMENTS

| | | |
|---|---|---|
| 6,430,752 B1 | 8/2002 | Bay |
| D507,857 S | 8/2005 | Ota et al. |
| D508,304 S | 8/2005 | Ota et al. |
| D512,203 S | 12/2005 | Ota et al. |
| D512,812 S | 12/2005 | Ota et al. |
| D520,715 S | 5/2006 | Ota et al. |
| 7,476,185 B2 | 1/2009 | Drennan |
| 7,631,367 B2 | 12/2009 | Caillibotte et al. |
| 7,730,552 B2 | 6/2010 | Ota et al. |
| 7,758,481 B2 | 7/2010 | Drennan |
| 7,814,576 B2 * | 10/2010 | Nakazawa ......... A41D 13/0015 2/227 |
| 7,959,591 B2 * | 6/2011 | Powers ................. A61F 5/0104 128/869 |
| 8,118,764 B2 | 2/2012 | Christenhusz et al. |
| 8,123,590 B2 | 2/2012 | MacKinnon |
| 8,214,926 B2 | 7/2012 | Brown |
| 8,296,864 B2 * | 10/2012 | Torry ....................... A41D 1/08 2/69 |
| 8,832,863 B2 * | 9/2014 | Yang .................. A63B 21/0552 2/69 |
| 8,910,317 B2 * | 12/2014 | Decker .............. A41D 13/0002 2/227 |
| 9,144,252 B1 * | 9/2015 | Kostrzewski ............ A41D 1/08 |
| 2003/0009120 A1 * | 1/2003 | MacAllister .......... A61F 5/0193 602/23 |
| 2003/0028952 A1 * | 2/2003 | Fujii ....................... A41C 1/003 2/400 |
| 2004/0107479 A1 * | 6/2004 | Dicker ............... A41D 13/0015 2/227 |
| 2004/0255358 A1 * | 12/2004 | Ota .................... A41D 13/0015 2/69 |
| 2005/0010150 A1 | 1/2005 | Firsov |
| 2006/0074365 A1 * | 4/2006 | Brown ................. A61F 5/0193 602/24 |
| 2008/0120757 A1 * | 5/2008 | Nakazawa ......... A41D 13/0015 2/22 |
| 2008/0201830 A1 | 8/2008 | Ishida et al. |
| 2010/0088803 A1 * | 4/2010 | Orloff ................ A41D 13/0015 2/228 |
| 2010/0292622 A1 * | 11/2010 | Weissleder ............ A61F 5/0193 602/23 |
| 2011/0000005 A1 * | 1/2011 | Brown .................. A61F 5/0104 2/227 |
| 2011/0092866 A1 * | 4/2011 | Lartonoix ............. A61F 5/0193 602/23 |
| 2011/0209267 A1 | 9/2011 | Rush et al. |
| 2011/0314590 A1 * | 12/2011 | Perron ............... A41D 13/0017 2/227 |
| 2012/0100778 A1 * | 4/2012 | Cho ........................ A41D 1/06 450/95 |
| 2012/0184887 A1 | 7/2012 | Wynne et al. |
| 2013/0144199 A1 * | 6/2013 | Brondsted ............. A61F 5/0104 602/23 |
| 2014/0096301 A1 * | 4/2014 | Waller ..................... A41D 7/00 2/67 |

FOREIGN PATENT DOCUMENTS

| | | |
|---|---|---|
| CN | 1461190 A | 12/2003 |
| CN | 201104491 Y | 8/2008 |
| CN | 102098933 A | 6/2011 |
| DE | 20 2009 004 817 U1 | 9/2010 |
| EP | 1 342 4223 A1 | 9/2003 |
| JP | 2009007720 A | 1/2015 |
| WO | WO 2011/144698 * | 11/2011 |
| WO | 2012/098755 A1 | 7/2012 |

OTHER PUBLICATIONS

NZ 708881, "First Examination Report," dated Aug. 28, 2015, 3 pages.
AU2013358978, "First Examiner Report", dated Feb. 16, 2016, 3 pages.
CA2893919, "Office Action", dated Jun. 14, 2016, 4 pages.
CN201380065644.2, "Office Action", dated Mar. 21, 2016, 23 pages.
NZ708881, "Substantive Examination Report", dated Feb. 12, 2016.
AU2013358978, "Second Examination Report," dated Jun. 22, 2016, 4 pages.
JP2015-548020, "Office Action," dated Jul. 1, 2016, 5 pages.
NZ 708881, Third Examination Report, dated May 30, 2016, 3 pgs.
NZ 708881, Fourth Examination Report, dated Jul. 20, 2016, 2 pgs.
NZ 708881, Notice of Acceptance, dated Aug. 29, 2016, 1 pg.
CN 201380065644.2, Notice on Grant of Patent Right for Invention, dated Oct. 9, 2016, 6 pgs.
CA2893919, "Office Action," dated Jan. 31, 2017, 5 pages.
JP2015-548020, "Office Action," dated Apr. 4, 2017, 5 pages.

* cited by examiner

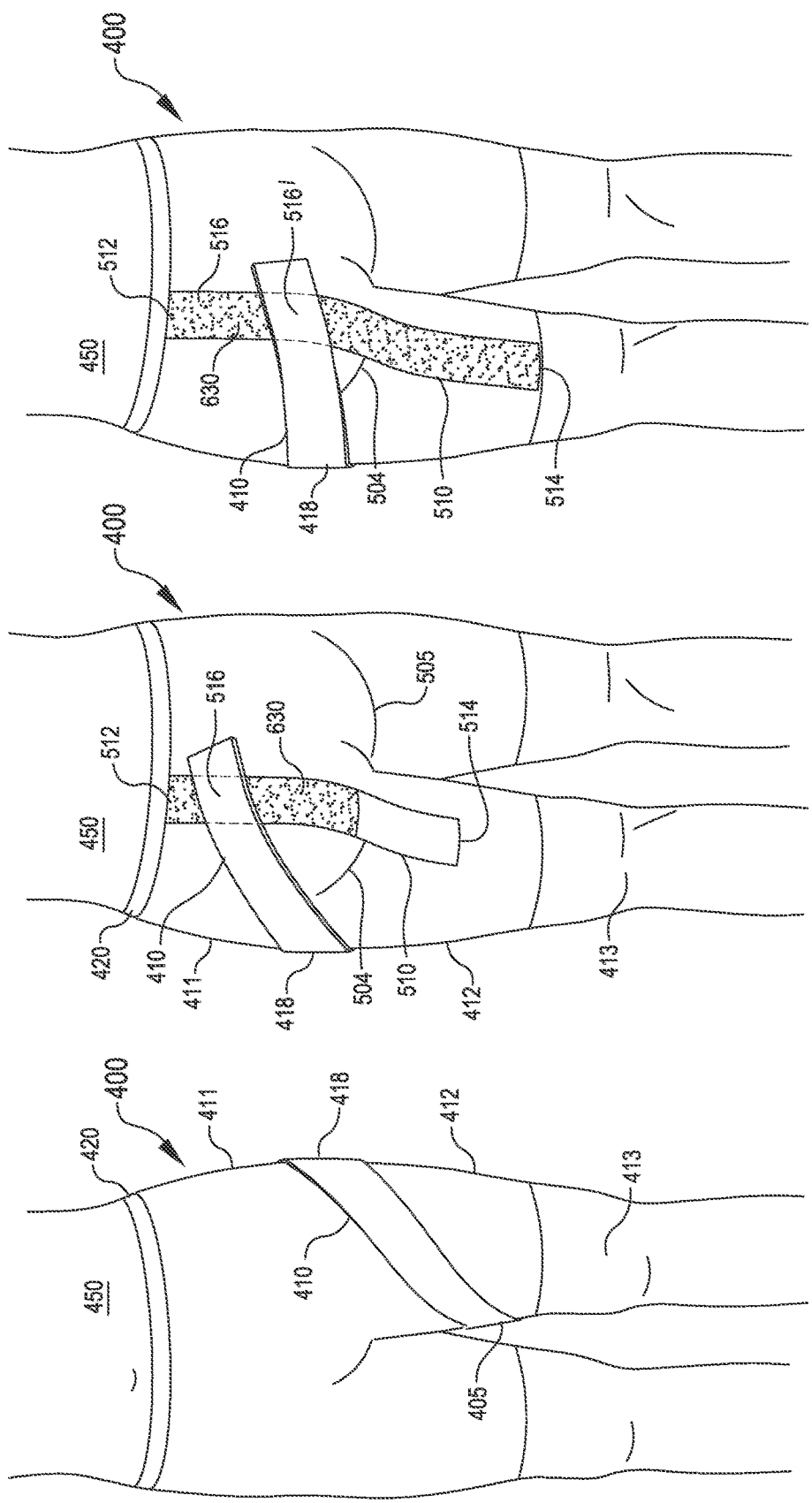

BRACE FOR PREVENTING SYMPTOMS OF FEMORAL ACETABULAR IMPINGEMENT

BACKGROUND OF THE INVENTION

Femoral acetabular impingement (FAI) is a condition affecting the ball and socket of a hip joint and surrounding soft tissues. Because FAI can lead to painful cartilage injuries, labral tears, and arthritis, methods of treatment or prevention are highly desirable.

FAI occurs when the femoral head rubs abnormally against or within the acetabular socket. Two principle types of FAI are recognized. Cam impingement occurs when one or more cam lesions on the femoral neck impinge on the acetabular rim during motion of the hip. Pincer impingement occurs when one or more pincer lesions on the acetabular rim produce an overcoverage of the acetabulum which repeatedly hits the femoral neck during motion of the hip. In many cases, both cam and pincer impingement are present.

Three primary motion types determine the orientation of the femoral neck to the acetabular rim and consequently affect the degree of femoral acetabular impingement experienced by a person during physical activity. As shown in FIG. 1A, these motions types are flexion 101, internal rotation 102, and adduction 103. Flexion 101 refers to the degree to which the leg is raised by the hip 111. Internal rotation 102 refers to the rotation of the thigh 112 toward the sagittal plane and the opposite thigh 122. Adduction refers to the lateral translation of the knee 113 toward the sagittal plane and the opposite knee 123. Any of these motions independently or the combination of these three movements occurring together can result in the femoral head contacting the acetabular rim at an anterior (either inward or outward) portion of the rim. Repeated contact can cause breakdown of the soft tissues and result in symptomatic femoral acetabular impingement.

BRIEF SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

A pair of compression shorts are disclosed for treating symptoms of femoral acetabular impingement and/or preventing the motions which cause the condition. The shorts have a number of connected yet distinguishable components or regions. A first garment leg is adapted to fit tightly to a first thigh of a wearer and to move with the first thigh when worn by the wearer during physical activity. The shorts also have a second garment leg, a waistline portion, and a buttocks portion connecting the first and second garment legs to the waistline on a posterior side of the shorts. Furthermore, the shorts include a groin portion connecting the first and second garment legs to the waistline on an anterior side of the shorts, wherein the groin portion extends around each hip of the wearer to meet the buttocks portion of the shorts. A first tension member comprising an elastic band is anchored to the first garment leg at a point corresponding to the lower inner first thigh of the wearer adjacent the wearer's knee. This first tension member extends diagonally around the anterior and lateral sides of the wearer's first thigh and is anchored to the buttocks portion of the garment. A second tension member comprising an elastic band is anchored to the first garment leg on the posterior side at a point below the buttocks. This second tension member extends along the posterior side of the garment and is anchored to a top portion of the buttocks portion of the garment.

The first tension member and the second tension member may be elastic bands. Each tension member may have a first end fixed to the garment and a second end detachably connectable to the garment. The second end may also be detachable from an initial point where the second end of the tension member is initially attached to the garment and reattachable to that initial point or to an alternate point to adjust at least one of the direction or magnitude of the tension in the tension member. The first tension member may also be attachable to the second tension member. The shorts may also be configured so that at least one end of the first tension member is detachably connectable to a same point on the garment as at least one end of the second tension member.

The shorts may also be configured so that the first tension member and the second tension member are made of material configured to stretch unidirectionally in a certain stretch direction. The shorts are designed so that the stretch direction is aligned to resist, when the garment is worn by a user, at least one of internal rotation of the thigh of the wearer, adduction of the knee of the wearer, or flexion of a hip of the wearer.

In some shorts, the second garment leg is adapted to fit tightly to a second thigh of a wearer and to move with the second thigh when worn by the wearer during physical activity. In these embodiments, the shorts have a third tension member, such as an elastic band, anchored to the second garment leg at a point corresponding to the lower inner second thigh of the wearer adjacent the wearer's second knee. The third tension member extends diagonally around the anterior and lateral sides of the wearer's second thigh and is anchored to the buttocks portion of the garment. A fourth tension member, such as an elastic band, is anchored to the second garment leg on the posterior side at a point below the buttocks. The fourth tension member extends along the posterior side of the garment and is anchored to a top portion of the buttocks portion of the garment.

The tension members may anchor at various points on the garment. For example, when the garment is worn by the wearer, at least one of the tension members may be anchored at or near the center of the buttocks portion of the garment or at or near the waistline portion of the garment. Alternatively, at least one of the tension members can be integrally formed into the garment.

A compression garment is disclosed having a sheath adapted to fit tightly to a thigh of a wearer and to move with the thigh when worn by the wearer. The garment has a first tension member extending from at least a lower inner thigh position on the sheath to at least an outer upper thigh position on the sheath. When the garment is worn by a wearer, the first tension member provides resistance to at least one of internal rotation of the thigh or adduction of the knee of the wearer. The garment also has a second tension member extending from at least a lower posterior position of the sheath to a higher posterior position of the sheath. When the garment is worn by a wearer, the second tension member provides resistance to flexion of a hip of the wearer. The garment may further have a buttocks portion of the garment, such that when the garment is worn by the wearer, at least one of the tension members extends to at least the buttocks portion of the garment.

A compression garment is also provided having a first garment leg adapted to adhere to a thigh of a wearer when the wearer is engaging in physical activity. The garment also has a first means connected to the first garment leg for limiting flexion of a wearer's hip and a second means connected to the first leg for limiting at least one of internal rotation of the wearer's thigh and adduction of the wearer's knee.

BRIEF DESCRIPTION OF THE DRAWINGS

FIG. 4 shows an anterior view of a compression garment incorporating tension straps attached to the shorts in accordance with various embodiments.

FIG. 5 shows a posterior view of the compression garment of FIG. 4.

FIG. 6 shows a posterior view of the compression shorts of FIGS. 4 and 5, showing an alternate configuration of first and second tension members.

DETAILED DESCRIPTION OF THE INVENTION

In the following description, various embodiments of the present invention will be described. For purposes of explanation, specific configurations and details are set forth in order to provide a thorough understanding of the embodiments. However, it will also be apparent to one skilled in the art that the present invention can be practiced without the specific details. Furthermore, well-known features may be omitted or simplified in order not to obscure the embodiment being described.

While engaged in exercise or physical activity, many athletes and physically active people tend to adduct and internally rotate their leg while it is raised as part of their gait or stride. As described above, the combination of these repeated motions of adduction, internal rotation, and flexion can bring the femoral neck and acetabular rim closer together. When a person has the anatomy of cam or pincer impingement, then these motions may result in breakdown of the soft tissues, essentially symptomatic FAI. The disclosure herein thus provides various garments, braces, and methods to dispose or bias the leg of a person against these motions while the person is engaged in activities, such as running, basketball, or other sports.

Figure 1A:
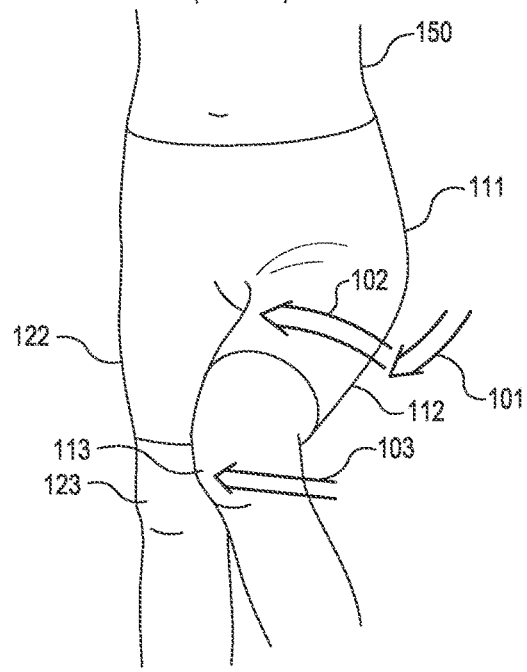
FIG. 1A shows a prior art anterior view of a person with leg motions contributing to FAI.
Figure 1B:
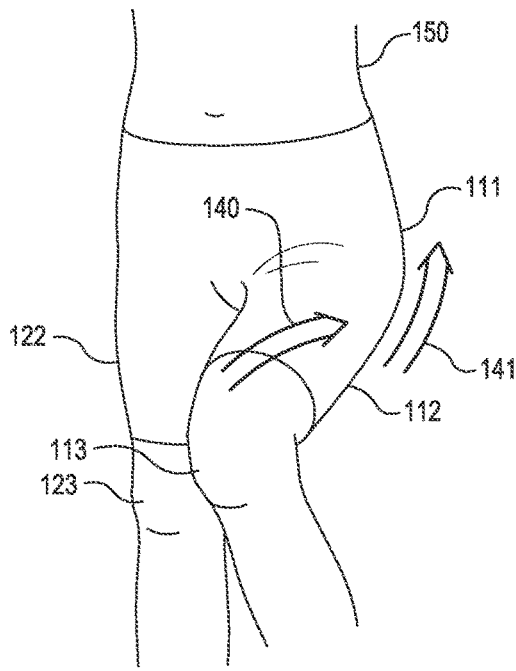
FIG. 1B shows an anterior view of a person and the forces applied to the person's body by tension members in various embodiments.

As shown in FIG. 1B, embodiments herein provide a first tension member anchored to the body 150 of a subject, and which produces a force 140 on the subject's body 150 to primarily limit the ability of the subject's thigh 112 to internally rotate 102 and the ability of the subject's knee 113 to adduct 103. Thus, this first tension member resists the tendency of the subject's leg to twist inward or deflect inward, each of which may contribute to FAI. Embodiments herein also provide a second tension member anchored to the subject's body 150, and which provides a force 141 to the subject's body 150 to primarily limit the ability of the subject's hip joint 111 to move in flexion 101. Thus, this second tension member resists the tendency of the subject's leg to raise too high, which may also contribute to FAI. The first and second tension members can each be used independent of the other, but embodiments utilize both on a single user so as to provide maximum protection for FAI.

Various embodiments for suitable tension members are available. In many embodiments, the tension member is a strip of stretchable material which resists stretching when expanded from an original length. The material may further exhibit a memory by which it returns toward its original length as the force applied to achieve the stretching subsides, with the material ultimately returning to its original length when the force has completely subsided. In such embodiments, when the tension member is properly anchored to the subject's body, the material's resistance to stretching provides the necessary force (e.g. 140 and/or 141) in the tension member to resist the subject's FAI-causing movements, i.e., as shown in FIG. 1A, at least one of internal rotation 102 of the thigh 112, adduction 103 of the knee 113, or flexion 101 at the hip 111. The memory causes the tension member to return toward its original orientation as the FAI-causing movement subsides. This places the tension member in a ready position to subsequently stretch and apply a force to resist FAI-causing movement of the subject's body when the subject next engages in such a subsequent FAI-causing movement. In this way, the tension member may cause resistance to the motions of the subject's body which are known to cause FAI without impeding the subject's overall ability to engage in physical activity. Put another way, the capability of the tension member to resist stretching to resist FAI-causing movement and return toward its original orientation as the FAI-causing movement subsides may correspond to the tension member or garment as a whole resisting movements in one direction or set of directions to a greater degree than the tension member or garment as a whole resists movement in an opposite direction or set of directions (e.g., the garment as a whole or part may resist internal rotation of the thigh of the wearer, adduction of the knee of the wearer, and flexion of the hip of the wearer to a greater degree than the garment as a whole or part resists external rotation of the thigh of the wearer, abduction of the knee of the wearer, and extension of the hip of the wearer). Elastic is one such material which exhibits these characteristics of stretchability and memory, and which would be suitable for constructing tension members of various embodiments. Unidirectional materials such as leno weave material, also known as gauze or doup weave, could also be used as tension members. This material stretches primarily in one direction, but allows very limited stretching in another. However, tension members need not be limited to the materials listed but may be made of any suitable material or combination of materials which may be configured to resist, when the tension member is anchored to a subject during physical activity, at least one of internal rotation 102 of the thigh 112, adduction 103 of the knee 113, or flexion 101 at the hip 111 of the subject 150.

The tension members can be provided in a way which ensures that the subject's body, and not merely the subject's clothing, receives the force applied by the tension members. One way to achieve this goal is to couple the tension members with a garment that fits tightly or snugly to the subject's body so that the garment stays in place relative to the subject's body even when the subject is engaged in physical activity. Such a tightly or snugly fitting garment can be formed, for example, of a garment of stretchable material with legs having relaxed-state cross-sections smaller than the legs of the subject but configured to expand to stretched-state cross-sections which conform and anchor to the legs of the subject when worn. For example, compression shorts, known in the art, may provide such a tightly fitting garment suitable for various embodiments. In accordance with further embodiments, any type of garment can be used that is adaptable to fit tightly to a wearer's body, including but not limited to pants, shorts, girdles, braces, full-body suits, and any variations of these such as crotchless, sleeveless, neckless, etc.

For example, in one embodiment, a pair of compression shorts or pants is provided having (1) a first tension strap that wraps around the wearer's thigh to limit adduction and internal rotation and (2) a second tension strap extending up the back of the wearer's buttocks and upper thigh to limit flexion during the wearer's physical activity. The straps can have ends that are either detachable or fixed to the shorts. The straps can attach to different points of the user's body or can travel over different paths across the body according to different embodiments. For example, one such path could include a first tension member anchoring on the inner knee of a leg, travelling diagonally up across the front of the thigh of the leg, and passing around to anchor somewhere on the buttocks above the back of the leg. As one alternative, a tension member could also achieve the same necessary magnitude and direction of force by an different orientation of the tension member such as attachment to the outer knee of a leg, wrapping diagonally across the backside of the thigh before passing around to the front of the same thigh and running upward to anchor at the hip of the same leg. Thus those skilled in the art may appreciate the diversity of orientations of tension members which may provide the necessary magnitude and direction of force upon the wearer's body.

In further embodiments, a pair of compression shorts is provided. An elastic band extends from a point on the shorts adjacent the knee on the inner thigh of the wearer, wraps diagonally upward across the anterior of the thigh, passes around the outer exterior of the upper thigh, proceeds diagonally up across the buttocks, and anchors to or adjacent to the waistband of the shorts near the wearer's spine. The tension of this band exerts a force on the wearer's leg that biases the leg against adduction of the knee and against internal rotation of the thigh. A second band extends from a point on the shorts adjacent the knee on the posterior of the thigh and proceeds up the back of the thigh and over the buttocks to an anchor point on or adjacent to the waistband of the shorts. The tension of this second band exerts a force on the wearer's leg that biases the leg against raising too high and thus limits the flexion experienced in the hip joint of the wearer. The combination of these exerted forces helps prevent the wearer's leg from the combined motion which leads to FAI, namely, adducting and rotating internally while in flexion.

Figure 2:
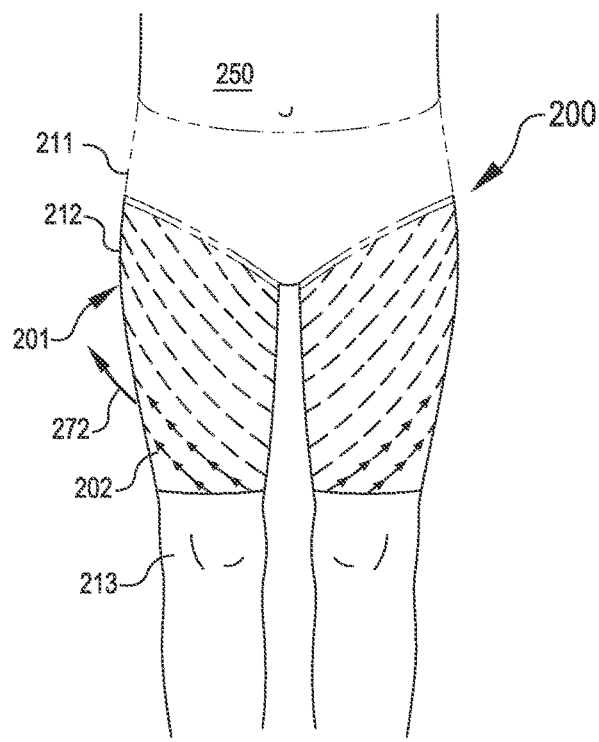
FIG. 2 shows an anterior view of compression shorts incorporating unidirectional material that is used for tension members in accordance with various embodiments.
Figure 3:
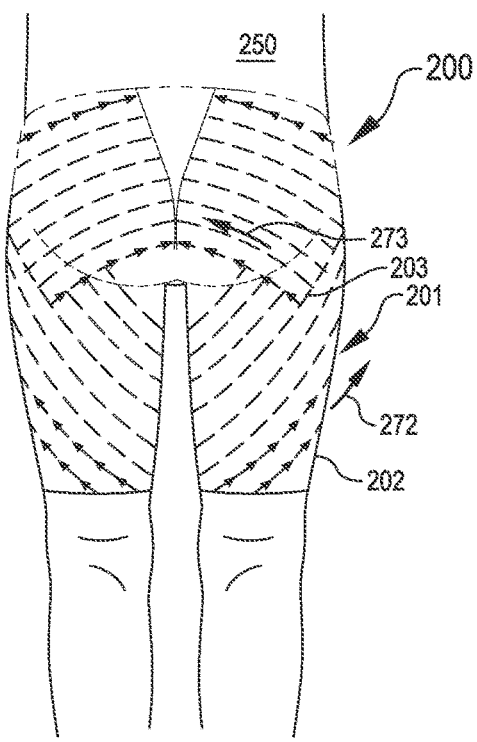
FIG. 3 shows a posterior view of the compression shorts of FIG. 2.

FIG. 2 shows an anterior view of various embodiments wherein unidirectional material is used as the first tension member 202. Garment 200 has a pant leg portion 201 containing first unidirectional tension member 202 aligned to stretch unidirectionally in a stretch direction 272 to resist internal rotation 102 and adduction 103 when the garment 200 is worn by a wearer 250 during physical activity. By way of example, for additional reference, a hip 211, a thigh 212, and a knee 213 of the wearer 250 are identified in FIG. 2. Preferred unidirectional materials include leno weave material, also known as gauze or doup weave. FIG. 3 shows a posterior view of various embodiments wherein unidirectional material is used as the tension members 202 and 203. In addition to first unidirectional tension member 202, garment 200 also has second unidirectional tension member 203 aligned to stretch unidirectionally in a stretch direction 273 to resist flexion 101 and adduction 103 when the garment 200 is worn by a wearer 250 during physical activity.

FIG. 4 shows an anterior view of garment 400 and another embodiment for a first tension member 410. In this embodiment, the first tension member 410 is an elastic band. In the embodiment shown, the first tension member 410 extends through a point 405 on the garment 400 located on the lower inner side of thigh 412 adjacent knee 413, wraps diagonally across the anterior of thigh 412, and passes around to the rear of wearer 450 at a point 418 on the outer upper side of thigh 412. However, the exact location of points 405 and 418 on garment 400 may differ in other embodiments so long as the location results in first tension member 410 providing resistance to at least one of internal rotation 102 of thigh 412 of wearer 450, adduction 103 of knee 413 of wearer 450, and flexion 101 of hip 411 of wearer 450 while wearer 450 is engaged in physical activity. For example, point 405 on garment 400 could be located anywhere up to the middle inner side of thigh 412. Alternatively, point 405 on garment 400 could also be located at any point across the lower anterior side of thigh 412 above knee 413. Similarly, point 418 could alternatively be placed anywhere down to the middle outer side of thigh 412 or up to waistband 420.

FIG. 5 shows a posterior view of garment 400 and a possible configuration of the first tension member 410 and second tension member 510. In the embodiment shown, first tension member 410 at point 418 passes around to the rear of the wearer 450 and attaches to garment 400 at point 516. Second tension member 510 extends through a point 514 on the garment 400 adjacent knee 413 on the rear of thigh 412 and proceeds up the back of thigh 412 and over buttocks 504 to attach to the garment 400 at point 512.

However, the exact placement of point 516 on garment 400 also (like point 418, discussed above) may differ in other embodiments so long as the placement results in first tension member 410 providing resistance to at least one of internal rotation 102 of thigh 412 of wearer 450, adduction 103 of knee 413 of wearer 450, and flexion 101 of hip 411 of wearer 450 while wearer 450 is engaged in physical activity. For example, as shown in FIG. 5, point 516 may be located at approximately the center of buttocks 504. Alternatively, point 516 could also be located anywhere else on buttocks 504, anywhere on buttocks 505, or anywhere elsewhere on the posterior side of garment 400, including on waistband 420.

Similarly, the exact placement of points 512 and 514 on garment 400 may differ in other embodiments so long as the placement results in second tension member 510 providing resistance to at least one of internal rotation 102 of thigh 412 of wearer 450, adduction 103 of knee 413 of wearer 450, and flexion 101 of hip 411 of wearer 450 while wearer 450 is engaged in physical activity. For example, point 514 could be located anywhere between the posterior of knee 413 and the bottom of buttocks 504. Similarly, point 512 could be located anywhere up to a point on waistband 420 or down to a point on the rear of thigh 412 just below the bottom of buttocks 504. Points 512 and 514 could also be on opposite sides of the posterior of garment 400; for example, if point 514 were on the rear side of thigh 412 below buttocks 504 and point 512 were attached to waistband 420 above buttocks 505.

FIG. 6 shows a posterior view of garment 400 and an alternate possible configuration of first tension member 410 and second tension member 510. In the embodiment shown, first tension member 410 attaches to garment 400 by a hook and loop fastener strip 630 which is affixed to the back of second tension member 510. First tension member 410 may thus be detached from garment 400 at point 516 on hook and loop fastener loop strip 630 and reattached to garment 400 at point 516 or at alternate point 516' on hook and loop fastener strip 630. Generally, tension members 410 and 510 may be detachable and attachable to garment 400 by any means known in the art including, but not limited to, a hook and loop fastener system (such as that sold under the trade name VELCRO), snaps, hooks, and buttons. Such detachability may improve ease of donning garment 400. Another benefit of such detachability may be that it provides a means to adjust the tension applied by either of tension members 410 and 510 or both.

Alternatively, tension members 410 and 510 may instead be fixed to garment 400. Such fixation may provide easier fabrication of garment 400 or improved calibration of tension provided by tension members 410 and 510.

Additionally, tension members 410 and 510 may be configured to have at least one point fixed to garment 400 and at least one other point which is detachable and reattachable to garment 400. For example, in one such embodiment, first tension member 410 would be fixed to garment 400 at point 405 and detachable and reattachable from garment 400 at point 516 while second tension member 510 would be detachable and reattachable at both points 512 and 514. Regardless of whether fixed, detachable and reattachable, or some combination thereof, tension members 410 and 510 may also have alternative means of adjusting the length and/or tension of the tension member. Tension members 410 and 510 may also be detachable and attachable to each other.

Tension members 410 and 510 may also attach to the same point on garment 400. For example, points 512 and 516 may correspond to the same or different points on garment 412.

Embodiments may also be applied independently to each leg or may be utilized in a combined garment which acts on both legs simultaneously. Embodiments may provide tension members to both legs or to only one leg. Furthermore, embodiments can provide differing levels of tension to each leg. The garment style also need not be the same for both legs. For example, a garment with one leg extending to the ankle of the subject and the other leg extending only midway down the thigh of the subject would not depart from providing many of the advantageous functions described herein.

The tension members may also be integrated into the garment as shown in FIG. 2-3, or the tension members may be of a separate piece from the garment as shown in FIG. 4-6. For example, in FIG. 4, tension member 410 is of a separate piece from the garment 400.

The following brief clarification of terms may assist the reader. As used herein, the term "Inner" indicates a relative location medial or proximate to the sagittal plane, as opposed to "outer," which instead indicates a relative location lateral or distal to the sagittal plane. If an object is "adjacent" to a thing, at least some part of the object is within a 10 inch radius of at least some part of the thing. The "middle" of an object refers to a region having a radius of approximately 10 inches emanating from the midpoint between the two extremes of the object.

Other variations are within the spirit of the invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A compression garment comprising:
    an anterior side of the garment;
    a posterior side of the garment;
    a waistband portion of the garment, the waistband portion extending at least partially along the anterior side and at least partially along the posterior side, the waistband portion corresponding to an upper extremity of the garment;
    a pant leg portion forming at least a portion of the anterior side of the garment and at least a portion of the posterior side of the garment, the pant leg portion adapted to fit tightly to a thigh of a wearer and to move with the thigh when the garment is worn by the wearer;

a first tension member extending from at least a lower inner thigh position of the pant leg portion to at least an outer upper thigh position of the pant leg portion; and a second tension member extending at least partially upward along the posterior side of the garment body when the garment is worn by the wearer and terminating at or adjacent the waistband portion when the garment is worn by the wearer, wherein, when the garment is worn by the wearer, the first tension member and the second member act on the garment so that the garment as a whole resists internal rotation of the thigh of the wearer, adduction of a knee of the wearer, and flexion of a hip of the wearer to a greater degree than the garment as a whole resists external rotation of the thigh of the wearer, abduction of the knee of the wearer, and extension of the hip of the wearer.

2. The garment of claim 1 further comprising a buttocks portion of the garment, wherein, when the garment is worn by the wearer, at least one of the tension members extends to at least the buttocks portion of the garment.

3. The garment of claim 2, wherein, when the garment is worn by the wearer, at least one of the tension members is anchored at or near the center of the buttocks portion of the garment.

4. The garment of claim 1, wherein, when the garment is worn by the wearer, at least one of the tension members is anchored at or near a waistline of the garment.

5. The garment of claim 1 wherein at least one of the tension members comprises material configured to stretch unidirectionally in a stretch direction aligned to resist, when the garment is worn by a user, at least one of internal rotation of the thigh of the wearer, adduction of the knee of the wearer, or flexion of a hip of the wearer.

6. The garment of claim 1 wherein at least one of the tension members is integrally formed into the garment.

7. The garment of claim 1 wherein, when the garment is worn by the wearer, the first tension member acts on the garment so as to resist internal rotation of the thigh of the wearer and adduction of the knee of the wearer.

8. The garment of claim 1 wherein, when the garment is worn by the wearer, the second tension member acts on the garment so as to resist adduction of the knee of the wearer and flexion of the hip of the wearer.

* * * * *